US012017050B2

(12) United States Patent
Snyder

(10) Patent No.: US 12,017,050 B2
(45) Date of Patent: *Jun. 25, 2024

(54) DRUG DEPOT DELIVERY SYSTEM AND METHOD

(71) Applicant: Warsaw Orthopedic, Inc., Warsaw, IN (US)

(72) Inventor: Lloyd M. Snyder, Collierville, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/048,783

(22) Filed: Oct. 21, 2022

(65) Prior Publication Data

US 2023/0128733 A1 Apr. 27, 2023

Related U.S. Application Data

(63) Continuation of application No. 16/590,654, filed on Oct. 2, 2019, now Pat. No. 11,478,587, which is a
(Continued)

(51) Int. Cl.
*A61M 5/315* (2006.01)
*A61K 9/00* (2006.01)
*A61M 37/00* (2006.01)

(52) U.S. Cl.
CPC ....... *A61M 5/31566* (2013.01); *A61K 9/0024* (2013.01); *A61M 5/315* (2013.01); *A61M 37/0069* (2013.01)

(58) Field of Classification Search
CPC .. A61M 2005/2411; A61M 2005/2414; A61M 2005/005; A61M 2005/2403;
(Continued)

(56) References Cited

U.S. PATENT DOCUMENTS 797,183 A 10/1904 Davis
1,881,854 A 10/1932 Muir
(Continued)

FOREIGN PATENT DOCUMENTS

CN 102056564 5/2011
CN 205073422 3/2016
(Continued)

OTHER PUBLICATIONS

Abd-Elsayed et al., "A Double-Blind Randomized Controlled Trial Comparing Epidural Clonidine vs Bupivacaine for Pain Control During and After Lower Abdominal Surgery", The Ochsner Journal, 2015, vol. 15, pp. 133-142.
(Continued)

*Primary Examiner* — Kevin C Sirmons
*Assistant Examiner* — Alexandra Lalonde
(74) *Attorney, Agent, or Firm* — Fletcher Yoder P.C.

(57) ABSTRACT

A drug depot delivery system includes a housing having a cavity. A cartridge is positioned within the cavity and includes a body having a channel. The body includes a first pair of rails and a second pair of rails. A plunger is slidably disposed in the housing and the cartridge. The plunger is configured to move a drug depot through the channel and out of the housing. Kits and methods of use are disclosed.

15 Claims, 8 Drawing Sheets

Related U.S. Application Data continuation of application No. 15/345,764, filed on Nov. 8, 2016, now Pat. No. 10,434,261.

(58) Field of Classification Search
CPC .. A61M 2005/2407; A61M 2005/2485; A61M 2005/1586; A61M 5/31566; A61M 5/315; A61M 5/31501; A61M 5/31505; A61M 5/31565; A61M 5/204; A61M 5/28; A61M 5/31; A61M 31/00; A61M 31/007; A61M 37/00; A61M 37/0069; A61M 2202/0007; A61M 2202/06; A61M 2025/0063; A61M 2025/0175; A61M 25/0097; A61M 25/0102; A61M 5/31596; A61M 5/2422; A61N 5/1007; A61N 2005/101; A61N 2005/1012; A61D 7/00; A61K 9/0024; A61B 17/3468; A61B 2090/3987; A61B 2017/00969

See application file for complete search history.

(56) References Cited

U.S. PATENT DOCUMENTS

| | | |
|---|---|---|
| 2,502,909 A | 4/1950 | Wick et al. |
| 2,513,014 A | 6/1950 | Fields |
| 2,751,907 A | 6/1956 | Hickey |
| 2,883,984 A | 4/1959 | Candido, Jr. et al. |
| 3,016,895 A | 1/1962 | Sein |
| 3,520,299 A | 7/1970 | Tapper et al. |
| 3,620,216 A | 11/1971 | Szymanski |
| 4,044,989 A | 8/1977 | Basel et al. |
| 4,069,825 A | 1/1978 | Akiyama |
| 4,105,030 A | 8/1978 | Kercso |
| 4,164,560 A | 8/1979 | Folkman et al. |
| D262,156 S | 12/1981 | Grubelnig |
| 4,344,431 A | 8/1982 | Yolles |
| 4,346,709 A | 8/1982 | Schmitt |
| 4,402,308 A | 9/1983 | Scott |
| 4,427,015 A | 1/1984 | Redeaux |
| 4,451,253 A | 5/1984 | Harman |
| 4,516,593 A | 5/1985 | Muto |
| 4,525,156 A | 6/1985 | Benusa et al. |
| 4,531,938 A | 7/1985 | Kaye et al. |
| 4,559,054 A | 12/1985 | Bruck |
| 4,576,591 A | 3/1986 | Kaye et al. |
| 4,624,255 A | 11/1986 | Schenck et al. |
| 4,624,848 A | 11/1986 | Lee |
| 4,700,692 A | 10/1987 | Baumgartner |
| 4,742,054 A | 5/1988 | Naftchi |
| 4,762,515 A | 8/1988 | Grimm |
| 4,774,091 A | 9/1988 | Yamahira et al. |
| 4,781,695 A | 11/1988 | Dalton |
| 4,791,939 A | 12/1988 | Maillard |
| 4,819,684 A | 4/1989 | Zaugg et al. |
| 4,820,267 A | 4/1989 | Harman |
| 4,820,284 A | 4/1989 | Hauri |
| 4,855,335 A | 8/1989 | Neperud |
| 4,863,457 A | 9/1989 | Lee |
| 4,871,094 A | 10/1989 | Gall et al. |
| 4,892,538 A | 1/1990 | Patrick et al. |
| 4,900,304 A | 2/1990 | Fujioka et al. |
| 4,909,250 A | 3/1990 | Smith |
| 4,936,827 A | 6/1990 | Grimm et al. |
| 4,941,874 A | 7/1990 | Sandow et al. |
| 5,024,655 A | 6/1991 | Freeman et al. |
| 5,024,841 A | 6/1991 | Chu et al. |
| 5,131,401 A | 7/1992 | Westenskow et al. |
| D328,644 S | 8/1992 | Pericic |
| 5,135,493 A | 8/1992 | Peschke |
| 5,163,904 A | 11/1992 | Lampropoulos et al. |
| 5,180,716 A | 1/1993 | Yaksh et al. |
| 5,183,470 A | 2/1993 | Wettermann |
| 5,196,015 A | 3/1993 | Neubardt |
| 5,207,678 A | 5/1993 | Harms et al. |
| 5,212,162 A | 5/1993 | Missel et al. |
| 5,236,426 A | 8/1993 | Schottes et al. |
| 5,284,479 A | 2/1994 | De Jong |
| 5,312,351 A | 5/1994 | Gerrone |
| 5,330,768 A | 7/1994 | Park et al. |
| 5,337,735 A | 8/1994 | Salerno |
| D353,668 S | 12/1994 | Banks |
| 5,391,081 A | 2/1995 | Lampotang et al. |
| D362,064 S | 9/1995 | Smick |
| 5,449,351 A | 9/1995 | Zohmann |
| 5,466,219 A | 11/1995 | Lynn et al. |
| 5,474,558 A | 12/1995 | Neubardt |
| 5,484,403 A | 1/1996 | Yoakum et al. |
| 5,487,739 A | 1/1996 | Aebischer et al. |
| 5,514,101 A | 5/1996 | Schulz et al. |
| 5,520,660 A | 5/1996 | Loos et al. |
| 5,522,844 A | 6/1996 | Johnson |
| D373,823 S | 9/1996 | Baldwin |
| 5,558,637 A | 9/1996 | Allonen et al. |
| 5,571,882 A | 11/1996 | Velter |
| 5,622,940 A | 4/1997 | Ostroff et al. |
| 5,626,838 A | 5/1997 | Cavanaugh, Jr. |
| 5,633,002 A | 5/1997 | Stricker et al. |
| 5,694,920 A | 12/1997 | Abrams et al. |
| 5,695,463 A | 12/1997 | Cherif-Cheikh |
| 5,725,508 A | 3/1998 | Chanoch et al. |
| 5,733,572 A | 3/1998 | Unger et al. |
| 5,752,930 A | 5/1998 | Rise et al. |
| 5,756,127 A | 5/1998 | Grisoni et al. |
| 5,759,583 A | 6/1998 | Iwamoto et al. |
| 5,772,671 A | 6/1998 | Harmon |
| 5,827,234 A | 10/1998 | Loos et al. |
| 5,829,589 A | 11/1998 | Nguyen et al. |
| 5,830,130 A | 11/1998 | Janzen et al. |
| 5,834,001 A | 11/1998 | Dionne et al. |
| 5,868,789 A | 2/1999 | Huebner |
| 5,902,273 A | 5/1999 | Yang et al. |
| 5,928,130 A | 7/1999 | Schmidt |
| 5,928,158 A | 7/1999 | Aristides |
| 5,942,241 A | 8/1999 | Chasin et al. |
| 5,980,927 A | 11/1999 | Nelson et al. |
| 6,001,386 A | 12/1999 | Ashton et al. |
| 6,007,843 A | 12/1999 | Drizen et al. |
| 6,015,557 A | 1/2000 | Tobinick et al. |
| 6,036,978 A | 3/2000 | Gombotz et al. |
| 6,063,057 A | 5/2000 | Choh |
| 6,069,129 A | 5/2000 | Sandberg et al. |
| 6,083,534 A | 7/2000 | Wallach et al. |
| 6,086,614 A | 7/2000 | Mumme |
| 6,102,844 A | 8/2000 | Ravins et al. |
| 6,132,420 A | 10/2000 | Dionne et al. |
| 6,179,862 B1 | 1/2001 | Sawhney |
| 6,190,350 B1 | 2/2001 | Davis et al. |
| 6,193,692 B1 | 2/2001 | Harris et al. |
| 6,203,813 B1 | 3/2001 | Gooberman |
| 6,214,370 B1 | 4/2001 | Nelson et al. |
| 6,235,289 B1 | 5/2001 | Aoki et al. |
| 6,242,004 B1 | 6/2001 | Raul |
| 6,248,345 B1 | 6/2001 | Goldenheim et al. |
| 6,258,056 B1 | 7/2001 | Turley et al. |
| 6,273,877 B1 | 8/2001 | West et al. |
| 6,277,969 B1 | 8/2001 | Le et al. |
| 6,287,588 B1 | 9/2001 | Shih et al. |
| 6,298,256 B1 | 10/2001 | Meyer |
| 6,326,020 B1 | 12/2001 | Kohane et al. |
| 6,331,311 B1 | 12/2001 | Brodbeck et al. |
| 6,391,005 B1 | 5/2002 | Lum et al. |
| 6,413,245 B1 | 7/2002 | Yaacobi et al. |
| 6,428,804 B1 | 8/2002 | Suzuki et al. |
| 6,450,937 B1 | 9/2002 | Mercereau et al. |
| 6,461,631 B1 | 10/2002 | Dunn et al. |
| 6,471,688 B1 | 10/2002 | Harper et al. |
| 6,478,768 B1 | 11/2002 | Kneer |
| 6,478,776 B1 | 11/2002 | Rosenman et al. |
| 6,478,790 B2 | 11/2002 | Bardani |
| 6,488,649 B1 | 12/2002 | Lichten |
| 6,497,729 B1 | 12/2002 | Moussy et al. |
| 6,524,607 B1 | 2/2003 | Goldenheim et al. |
| 6,530,934 B1 | 3/2003 | Jacobsen et al. |

(56) References Cited

U.S. PATENT DOCUMENTS

| | | |
|---|---|---|
| 6,531,154 B1 | 3/2003 | Mathiowitz et al. |
| 6,534,081 B2 | 3/2003 | Goldenheim et al. |
| 6,551,290 B1 | 4/2003 | Elsberry et al. |
| 6,554,778 B1 | 4/2003 | Fleming |
| 6,565,541 B2 | 5/2003 | Sharp |
| 6,571,125 B2 | 5/2003 | Thompson |
| 6,582,441 B1 | 6/2003 | He et al. |
| 6,589,549 B2 | 7/2003 | Shih et al. |
| 6,594,880 B2 | 7/2003 | Elsberry |
| 6,616,946 B1 | 9/2003 | Meier et al. |
| 6,630,155 B1 | 10/2003 | Chandrashekar et al. |
| 6,632,457 B1 | 10/2003 | Sawhney |
| 6,648,849 B2 | 11/2003 | Tenhuisen et al. |
| 6,652,883 B2 | 11/2003 | Goupil et al. |
| 6,673,333 B1 | 1/2004 | Meade et al. |
| 6,676,971 B2 | 1/2004 | Goupil et al. |
| 6,710,126 B1 | 3/2004 | Hirt et al. |
| 6,723,741 B2 | 4/2004 | Jeon et al. |
| 6,723,814 B2 | 4/2004 | Meier et al. |
| 6,735,475 B1 | 5/2004 | Whitehurst et al. |
| 6,756,058 B2 | 7/2004 | Brubaker et al. |
| 6,773,714 B2 | 8/2004 | Dunn et al. |
| 6,837,865 B2 | 1/2005 | Kneer |
| 6,869,426 B2 | 3/2005 | Ganem |
| 6,916,308 B2 | 7/2005 | Dixon et al. |
| 6,921,541 B2 | 7/2005 | Chasin et al. |
| 6,936,270 B2 | 8/2005 | Watson et al. |
| 6,971,998 B2 | 12/2005 | Rosenman et al. |
| 6,974,462 B2 | 12/2005 | Sater |
| 6,982,089 B2 | 1/2006 | Tobinick |
| 6,993,375 B2 | 1/2006 | Burbank et al. |
| 7,001,892 B1 | 2/2006 | Chmielewski et al. |
| 7,012,106 B2 | 3/2006 | Yuan et al. |
| 7,018,384 B2 | 3/2006 | Skakoon |
| 7,070,583 B1 | 7/2006 | Higuchi et al. |
| 7,070,809 B2 | 7/2006 | Goupil et al. |
| 7,081,123 B2 | 7/2006 | Merboth et al. |
| 7,108,153 B2 | 9/2006 | Wood |
| 7,144,412 B2 | 12/2006 | Wolf et al. |
| 7,166,570 B2 | 1/2007 | Hunter et al. |
| 7,204,826 B2 | 4/2007 | Tremaglio et al. |
| 7,212,865 B2 | 5/2007 | Cory |
| 7,215,426 B2 | 5/2007 | Tsuyuki et al. |
| 7,220,281 B2 | 5/2007 | Lambrecht et al. |
| 7,223,289 B2 | 5/2007 | Trieu et al. |
| 7,229,441 B2 | 6/2007 | Trieu et al. |
| 7,235,043 B2 | 6/2007 | Gellman et al. |
| 7,252,651 B2 | 8/2007 | Haider et al. |
| 7,252,685 B2 | 8/2007 | Bindseil et al. |
| 7,276,477 B2 | 10/2007 | Osslund et al. |
| 7,287,983 B2 | 10/2007 | Ilan |
| 7,302,960 B2 | 12/2007 | Patzer |
| 7,317,091 B2 | 1/2008 | Lazar et al. |
| 7,318,840 B2 | 1/2008 | McKay |
| D561,896 S | 2/2008 | Jones |
| 7,329,259 B2 | 2/2008 | Cragg |
| 7,344,716 B2 | 3/2008 | Di Mauro et al. |
| 7,355,008 B2 | 4/2008 | Stavenhagen et al. |
| 7,357,792 B2 | 4/2008 | Newton et al. |
| 7,361,168 B2 | 4/2008 | Makower et al. |
| 7,367,978 B2 | 5/2008 | Drewry et al. |
| D571,463 S | 6/2008 | Chesnin |
| 7,400,930 B2 | 7/2008 | Sharkey et al. |
| 7,585,280 B2 | 9/2008 | Wilson et al. |
| 7,618,370 B2 | 11/2009 | Choi et al. |
| D606,190 S | 12/2009 | Pruitt |
| 7,637,279 B2 | 12/2009 | Amley et al. |
| 7,700,100 B2 | 4/2010 | Johnson et al. |
| D616,095 S | 5/2010 | Kim |
| 7,727,954 B2 | 6/2010 | McKay |
| 7,741,273 B2 | 6/2010 | McKay |
| D624,653 S | 9/2010 | Boillat |
| 7,798,988 B2 | 9/2010 | Aubert et al. |
| D630,733 S | 1/2011 | Ahlgren |
| 7,955,301 B1 | 6/2011 | McKay |
| 7,998,108 B2 | 8/2011 | Nazzaro et al. |
| 8,029,458 B2 | 10/2011 | Cherif-Cheikh et al. |
| 8,029,478 B2 | 10/2011 | Zanella |
| 8,084,582 B2 | 12/2011 | Dahiyat et al. |
| 8,088,119 B2 | 1/2012 | Saal et al. |
| 8,092,424 B2 | 1/2012 | Mueller et al. |
| 8,221,358 B2 | 7/2012 | McKay |
| 8,246,571 B2 | 8/2012 | Simonton et al. |
| 8,267,895 B2 | 9/2012 | McKay |
| 8,337,453 B2 | 12/2012 | Lind |
| 8,357,388 B2 | 1/2013 | McKay |
| 8,481,064 B2 | 7/2013 | McKay |
| 8,485,180 B2 | 7/2013 | Smutney et al. |
| 8,585,655 B2 | 11/2013 | Bierman |
| 8,608,705 B2 | 12/2013 | Peters et al. |
| 8,652,092 B2 | 2/2014 | Bussmann |
| 8,702,677 B2 | 4/2014 | Simonton et al. |
| 8,715,223 B2 | 5/2014 | McKay |
| 8,790,293 B2 | 7/2014 | Nazzaro et al. |
| D711,542 S | 8/2014 | Pierson |
| 8,834,412 B2 | 9/2014 | Painchaud et al. |
| D715,929 S | 10/2014 | Khalaj |
| 8,992,458 B2 | 3/2015 | Singh et al. |
| 8,998,854 B2 | 4/2015 | McKay |
| 9,050,415 B2 | 6/2015 | Shetty et al. |
| D737,435 S | 8/2015 | Ha et al. |
| D751,702 S | 3/2016 | Eaton et al. |
| 9,271,754 B2 | 3/2016 | Ostrovsky et al. |
| 9,381,111 B2 | 7/2016 | Hickingbotham et al. |
| D782,037 S | 3/2017 | Osypka |
| 9,764,122 B2 | 9/2017 | Clay et al. |
| 9,775,978 B2 | 10/2017 | Clay et al. |
| D802,755 S | 11/2017 | Snyder |
| D802,756 S | 11/2017 | Snyder |
| D802,757 S | 11/2017 | Snyder et al. |
| 9,867,974 B2 | 1/2018 | Beebe et al. |
| D809,652 S | 2/2018 | Snyder et al. |
| 10,076,650 B2 | 9/2018 | Koch et al. |
| 10,080,877 B2 | 9/2018 | Clay et al. |
| 10,272,234 B2 | 4/2019 | Wetzel et al. |
| 10,342,966 B2 | 7/2019 | Shetty et al. |
| 10,384,048 B2 | 8/2019 | Clay et al. |
| 10,391,291 B2 | 8/2019 | Wallace et al. |
| 10,405,955 B2 | 9/2019 | Eisele et al. |
| 10,434,261 B2 | 10/2019 | Snyder |
| 10,478,603 B2 | 11/2019 | Clay et al. |
| 10,549,081 B2 | 2/2020 | Snyder |
| 10,668,262 B2 | 6/2020 | Jacome et al. |
| 10,856,907 B2 | 12/2020 | Virden |
| 10,940,300 B2 | 3/2021 | Mellejor et al. |
| 11,166,798 B2 | 11/2021 | Eisele et al. |
| 11,273,266 B2 | 3/2022 | Daftary et al. |
| 11,413,442 B2 | 8/2022 | Snyder |
| 11,464,958 B2 | 10/2022 | Clay et al. |
| 11,504,513 B2 | 11/2022 | Clay et al. |
| 11,646,958 B2 | 5/2023 | Charles et al. |
| 11,759,614 B2 | 9/2023 | Koch et al. |
| 2001/0005785 A1 | 6/2001 | Sachse |
| 2001/0020147 A1 | 9/2001 | Staniforth et al. |
| 2001/0031940 A1* | 10/2001 | Loos ............... A61M 37/0069 604/15 |
| 2001/0033867 A1 | 10/2001 | Ahern et al. |
| 2001/0043915 A1 | 11/2001 | Frey |
| 2002/0009454 A1 | 1/2002 | Boone et al. |
| 2002/0022800 A1 | 2/2002 | O'Holloran et al. |
| 2002/0077521 A1 | 6/2002 | Green et al. |
| 2002/0082583 A1 | 6/2002 | Lerner |
| 2002/0090398 A1 | 7/2002 | Dunn et al. |
| 2002/0116022 A1 | 8/2002 | Lebouitz et al. |
| 2002/0198527 A1 | 12/2002 | Muckter |
| 2003/0004491 A1 | 1/2003 | Tenhuisen et al. |
| 2003/0009235 A1 | 1/2003 | Manrique et al. |
| 2003/0023310 A1 | 1/2003 | Lubock et al. |
| 2003/0036673 A1 | 2/2003 | Schmidt |
| 2003/0039613 A1 | 2/2003 | Unger et al. |
| 2003/0045808 A1 | 3/2003 | Kaula et al. |
| 2003/0144570 A1 | 7/2003 | Hunter et al. |
| 2003/0171637 A1 | 9/2003 | Terwilliger et al. |
| 2003/0171954 A1 | 9/2003 | Guerin et al. |

(56) References Cited

U.S. PATENT DOCUMENTS

| | | |
|---|---|---|
| 2003/0185873 A1 | 10/2003 | Chasin et al. |
| 2003/0204191 A1 | 10/2003 | Sater et al. |
| 2003/0224033 A1 | 12/2003 | Li et al. |
| 2004/0015133 A1 | 1/2004 | Karim |
| 2004/0015149 A1 | 1/2004 | Palasis |
| 2004/0034357 A1 | 2/2004 | Beane et al. |
| 2004/0054338 A1 | 3/2004 | Bybordi et al. |
| 2004/0064088 A1 | 4/2004 | Gorman et al. |
| 2004/0064193 A1 | 4/2004 | Evans et al. |
| 2004/0065615 A1 | 4/2004 | Hooper et al. |
| 2004/0072799 A1 | 4/2004 | Li et al. |
| 2004/0082540 A1 | 4/2004 | Hermida Ochoa |
| 2004/0082908 A1 | 4/2004 | Whitehurst et al. |
| 2004/0098113 A1 | 5/2004 | Forsell et al. |
| 2004/0106914 A1 | 6/2004 | Coppeta et al. |
| 2004/0109893 A1 | 6/2004 | Chen et al. |
| 2004/0111118 A1 | 6/2004 | Hill et al. |
| 2004/0162574 A1 | 8/2004 | Viola |
| 2004/0214793 A1 | 10/2004 | Hermida Ochoa |
| 2004/0220545 A1 | 11/2004 | Heruth et al. |
| 2004/0220546 A1 | 11/2004 | Heruth et al. |
| 2004/0220547 A1 | 11/2004 | Heruth et al. |
| 2004/0220548 A1 | 11/2004 | Heruth et al. |
| 2004/0228901 A1 | 11/2004 | Trieu et al. |
| 2004/0229878 A1 | 11/2004 | DiMauro et al. |
| 2004/0249464 A1 | 12/2004 | Bindseil et al. |
| 2005/0025765 A1 | 2/2005 | DiMauro et al. |
| 2005/0043673 A1 | 2/2005 | Lieberman |
| 2005/0070843 A1 | 3/2005 | Gonzales |
| 2005/0074481 A1 | 4/2005 | Brekke et al. |
| 2005/0079202 A1 | 4/2005 | Chen et al. |
| 2005/0107756 A1 | 5/2005 | McCraw |
| 2005/0137579 A1 | 6/2005 | Heruth et al. |
| 2005/0142163 A1 | 6/2005 | Hunter et al. |
| 2005/0143689 A1 | 6/2005 | Ramsey, III |
| 2005/0152905 A1 | 7/2005 | Omoigui |
| 2005/0152949 A1 | 7/2005 | Hotchkiss et al. |
| 2005/0175709 A1 | 8/2005 | Baty, III et al. |
| 2005/0177118 A1 | 8/2005 | Hoganson et al. |
| 2005/0177135 A1 | 8/2005 | Hildebrand et al. |
| 2005/0178779 A1 | 8/2005 | Wood |
| 2005/0184264 A1 | 8/2005 | Tesluk et al. |
| 2005/0186261 A1 | 8/2005 | Avelar et al. |
| 2005/0197293 A1 | 9/2005 | Mellis et al. |
| 2005/0203542 A1 | 9/2005 | Weber et al. |
| 2005/0245906 A1 | 11/2005 | Makower et al. |
| 2005/0249775 A1 | 11/2005 | Falotico et al. |
| 2005/0228620 A1 | 12/2005 | Shippert |
| 2005/0278023 A1 | 12/2005 | Zwirkoski |
| 2005/0287218 A1 | 12/2005 | Chaouk et al. |
| 2005/0288789 A1 | 12/2005 | Chaouk et al. |
| 2006/0046960 A1 | 3/2006 | McKay et al. |
| 2006/0046961 A1 | 3/2006 | McKay et al. |
| 2006/0074422 A1 | 4/2006 | Story et al. |
| 2006/0084943 A1 | 4/2006 | Roseman et al. |
| 2006/0100622 A1 | 5/2006 | Jackson |
| 2006/0106361 A1 | 5/2006 | Muni et al. |
| 2006/0121032 A1 | 6/2006 | Dahiyat et al. |
| 2006/0148903 A1 | 7/2006 | Burch et al. |
| 2006/0153815 A1 | 7/2006 | Seyda et al. |
| 2006/0161114 A1 | 7/2006 | Perot et al. |
| 2006/0183786 A1 | 8/2006 | Wang |
| 2006/0189944 A1 | 8/2006 | Campbell et al. |
| 2006/0228391 A1 | 10/2006 | Seyedin et al. |
| 2006/0253100 A1 | 11/2006 | Burright et al. |
| 2006/0264839 A1 | 11/2006 | Veasey et al. |
| 2007/0005005 A1 | 1/2007 | Wang |
| 2007/0021358 A1 | 1/2007 | Edelman et al. |
| 2007/0043359 A1 | 2/2007 | Altarac et al. |
| 2007/0055378 A1 | 3/2007 | Ankney et al. |
| 2007/0066864 A1 | 3/2007 | Forde |
| 2007/0104769 A1 | 5/2007 | Feng et al. |
| 2007/0106247 A1 | 5/2007 | Burnett et al. |
| 2007/0118142 A1 | 5/2007 | Krueger et al. |
| 2007/0123863 A1 | 5/2007 | Winslow et al. |
| 2007/0129744 A1 | 6/2007 | Teichert et al. |
| 2007/0149992 A1 | 6/2007 | Teng |
| 2007/0156180 A1 | 7/2007 | Jaax et al. |
| 2007/0179474 A1 | 8/2007 | Cahill et al. |
| 2007/0185497 A1 | 8/2007 | Cauthen et al. |
| 2007/0202074 A1 | 8/2007 | Shalaby |
| 2007/0219564 A1 | 9/2007 | Rue et al. |
| 2007/0233038 A1 | 10/2007 | Pruit et al. |
| 2007/0243225 A1 | 10/2007 | McKay |
| 2007/0243228 A1 | 10/2007 | McKay |
| 2007/0244442 A1 | 10/2007 | Chowhan |
| 2007/0248639 A1 | 10/2007 | Demopulos et al. |
| 2007/0249632 A1 | 10/2007 | Zentner |
| 2007/0253994 A1 | 11/2007 | Hildebrand |
| 2007/0255281 A1 | 11/2007 | Simonton et al. |
| 2007/0255282 A1 | 11/2007 | Simonton et al. |
| 2007/0260184 A1 | 11/2007 | Justis et al. |
| 2007/0260201 A1 | 11/2007 | Prausnitz et al. |
| 2007/0265582 A1 | 11/2007 | Kaplan et al. |
| 2008/0004570 A1 | 1/2008 | Simonton et al. |
| 2008/0004703 A1 | 1/2008 | Trieu et al. |
| 2008/0009830 A1 | 1/2008 | Fujimoto et al. |
| 2008/0021074 A1 | 1/2008 | Cartt |
| 2008/0038351 A1 | 2/2008 | Beals et al. |
| 2008/0065029 A1 | 3/2008 | Racz |
| 2008/0077093 A1 | 3/2008 | Gratwohl et al. |
| 2008/0091207 A1 | 4/2008 | Truckai et al. |
| 2008/0097229 A1 | 4/2008 | Roy et al. |
| 2008/0102097 A1 | 5/2008 | Zanella |
| 2008/0125637 A1 | 5/2008 | Geist et al. |
| 2008/0139877 A1 | 6/2008 | Chu et al. |
| 2008/0208138 A1 | 8/2008 | Lim et al. |
| 2008/0215001 A1 | 9/2008 | Cowe |
| 2008/0228193 A1 | 9/2008 | Matityahu |
| 2008/0294039 A1 | 11/2008 | Jones et al. |
| 2009/0053211 A9 | 2/2009 | Lazar et al. |
| 2009/0088809 A1 | 4/2009 | Fisher et al. |
| 2009/0099597 A1 | 4/2009 | Isse |
| 2009/0148500 A1 | 6/2009 | Lawter et al. |
| 2009/0177141 A1 | 7/2009 | Kucklick |
| 2009/0182267 A1 | 7/2009 | Painchaud et al. |
| 2009/0209804 A1 | 8/2009 | Seiler et al. |
| 2009/0246123 A1 | 10/2009 | Zanella et al. |
| 2009/0263319 A1 | 10/2009 | Wohabrebbi et al. |
| 2009/0263321 A1 | 10/2009 | McDonald et al. |
| 2009/0263441 A1 | 10/2009 | McKay |
| 2009/0263459 A1 | 10/2009 | King et al. |
| 2009/0263460 A1 | 10/2009 | McDonald |
| 2009/0264490 A1 | 10/2009 | Zanella et al. |
| 2009/0264491 A1 | 10/2009 | McKay et al. |
| 2009/0270797 A1 | 10/2009 | Aubert et al. |
| 2010/0015049 A1 | 1/2010 | Wohabrebbi |
| 2010/0106132 A1 | 4/2010 | Simonton |
| 2010/0106136 A1 | 4/2010 | Simonton |
| 2010/0106137 A1 | 4/2010 | Simonton et al. |
| 2010/0160375 A1 | 6/2010 | King |
| 2010/0163059 A1 | 7/2010 | Tierney et al. |
| 2010/0198140 A1 | 8/2010 | Lawson |
| 2010/0249750 A1 | 9/2010 | Racz |
| 2010/0331868 A1 | 12/2010 | Bardy |
| 2010/0331874 A1 | 12/2010 | Bardy |
| 2011/0098675 A1* | 4/2011 | Schmalz ............ A61M 37/0069 604/60 |
| 2011/0104233 A1 | 5/2011 | Drapeau |
| 2011/0106110 A1 | 5/2011 | McKay |
| 2011/0152755 A1 | 6/2011 | Schmalz |
| 2011/0182849 A1 | 7/2011 | Haddock et al. |
| 2011/0202011 A1 | 8/2011 | Wozencrift |
| 2011/0313393 A1 | 12/2011 | Zanella |
| 2012/0022568 A1 | 1/2012 | Koblish et al. |
| 2012/0053561 A1* | 3/2012 | Simonton ......... A61M 37/0069 604/60 |
| 2012/0142648 A1 | 6/2012 | Biggs et al. |
| 2012/0142747 A1 | 6/2012 | Wilsey et al. |
| 2013/0116556 A1 | 5/2013 | Racz |
| 2013/0178822 A1 | 7/2013 | Hickingbotham et al. |
| 2013/0211328 A1 | 8/2013 | Plumptre et al. |
| 2013/0261596 A1 | 10/2013 | McKay |
| 2014/0277459 A1 | 9/2014 | McCarthy |

(56) References Cited

U.S. PATENT DOCUMENTS

| | | | |
|---|---|---|---|
| 2015/0238687 A1* | 8/2015 | Novakovic | A61F 9/0017 604/502 |
| 2016/0263364 A1 | 9/2016 | Eisele et al. | |
| 2016/0296739 A1 | 10/2016 | Cleveland | |
| 2016/0354115 A1 | 12/2016 | Smith et al. | |
| 2017/0231716 A1* | 8/2017 | Ahari | A61B 10/02 600/431 |
| 2017/0354811 A1 | 12/2017 | Clay et al. | |
| 2018/0001072 A1 | 1/2018 | Clay et al. | |
| 2018/0126090 A1 | 5/2018 | Snyder | |
| 2019/0015653 A1 | 1/2019 | Koch et al. | |
| 2019/0054253 A1 | 2/2019 | Kneer et al. | |
| 2019/0247638 A1 | 8/2019 | Murphy | |
| 2019/0255308 A1 | 8/2019 | Virden | |
| 2019/0262115 A1 | 8/2019 | Eisele et al. | |
| 2019/0374762 A1 | 12/2019 | Clay et al. | |
| 2020/0030545 A1 | 1/2020 | Snyder | |
| 2020/0078576 A1 | 3/2020 | Clay et al. | |
| 2020/0171291 A1 | 6/2020 | Snyder | |
| 2021/0000504 A1 | 1/2021 | Van Beek | |
| 2021/0236787 A1 | 8/2021 | Koch et al. | |
| 2021/0259736 A1 | 8/2021 | Hochmuth et al. | |
| 2021/0393935 A1 | 12/2021 | Richter et al. | |
| 2022/0062608 A1 | 3/2022 | Kneer et al. | |
| 2022/0117628 A1 | 4/2022 | Kuebler | |
| 2022/0143321 A1 | 5/2022 | Daftary et al. | |
| 2022/0143326 A1 | 5/2022 | Daftary et al. | |
| 2022/0203042 A1 | 6/2022 | Daftary et al. | |
| 2023/0149682 A1 | 5/2023 | Clay et al. | |

FOREIGN PATENT DOCUMENTS

| | | |
|---|---|---|
| DE | 1955059 | 2/1967 |
| DE | 19640670 | 5/1998 |
| EP | 0 548 612 | 6/1993 |
| EP | 1 216 721 | 6/2002 |
| EP | 1 323 450 | 9/2004 |
| EP | 1 518 549 | 2/2007 |
| EP | 1 625 870 | 5/2008 |
| EP | 2 008 596 | 12/2008 |
| EP | 3 010 575 | 7/2021 |
| EP | 3 493 864 | 9/2021 |
| FR | 1 270 590 | 9/1961 |
| FR | 2 007 684 | 1/1970 |
| FR | 2 231 355 | 12/1974 |
| GB | 1379358 | 1/1975 |
| JP | 2006-509531 | 3/2006 |
| JP | 2009-160395 | 7/2009 |
| JP | 2011-087940 | 5/2011 |
| KR | 10-2006-0120103 | 11/2006 |
| WO | WO 93/20859 | 10/1993 |
| WO | WO 94/01166 | 1/1994 |
| WO | WO 1999/052573 | 10/1999 |
| WO | WO 2000/038574 | 7/2000 |
| WO | WO 2001/062272 | 8/2001 |
| WO | WO 2002/034116 | 5/2002 |
| WO | WO 2002/085188 | 10/2002 |
| WO | WO 2003/005961 | 1/2003 |
| WO | WO 2004/009776 | 1/2004 |
| WO | WO 2004/050688 | 6/2004 |
| WO | WO 2004/084819 | 10/2004 |
| WO | WO 2005/018468 | 3/2005 |
| WO | WO 2005/034998 | 4/2005 |
| WO | WO 2007/121288 | 10/2007 |
| WO | WO 2008/067362 | 6/2008 |
| WO | WO 2008/091777 | 7/2008 |
| WO | WO 2009/049823 | 4/2009 |
| WO | WO 2009/134314 | 11/2009 |
| WO | WO 2010/011526 | 1/2010 |
| WO | WO 2016/014300 | 1/2016 |
| WO | WO 2019/028138 | 2/2019 |
| WO | WO 2019/125457 | 6/2019 |

OTHER PUBLICATIONS

European Search Report for counterpart application dated Mar. 12, 2018, 8 pages.

* cited by examiner

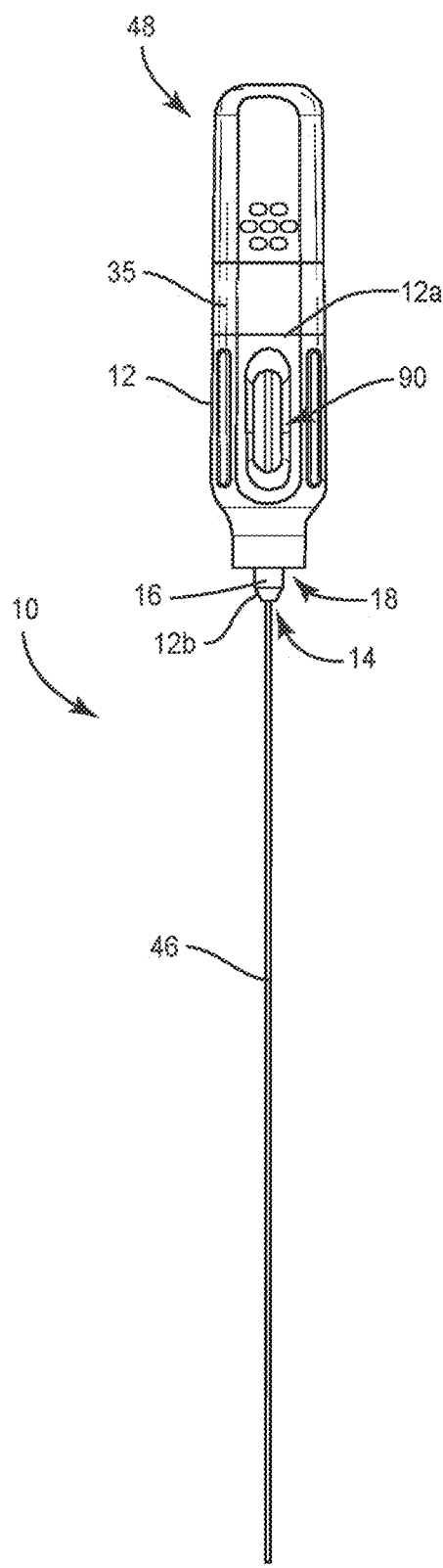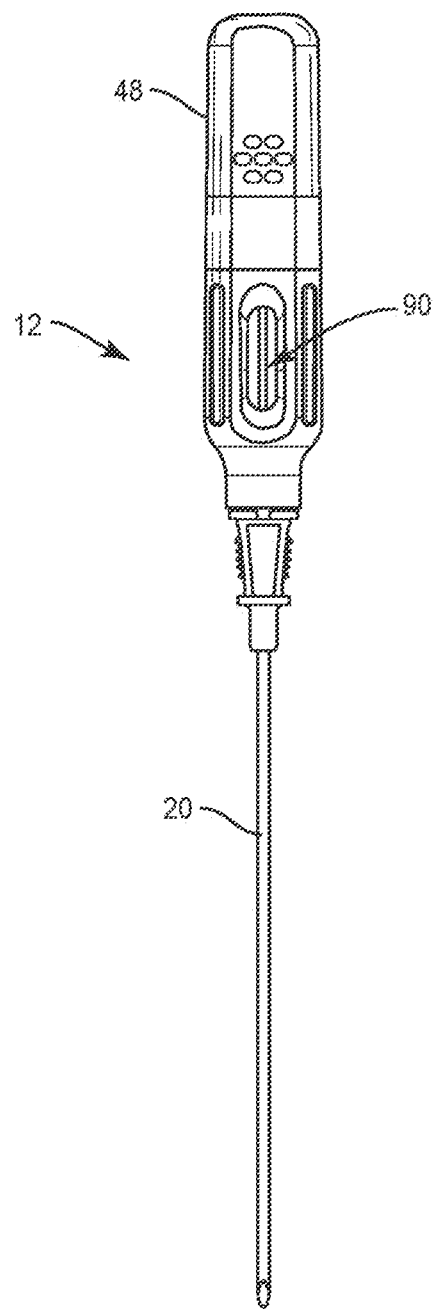
*FIG. 1*  *FIG. 1A*

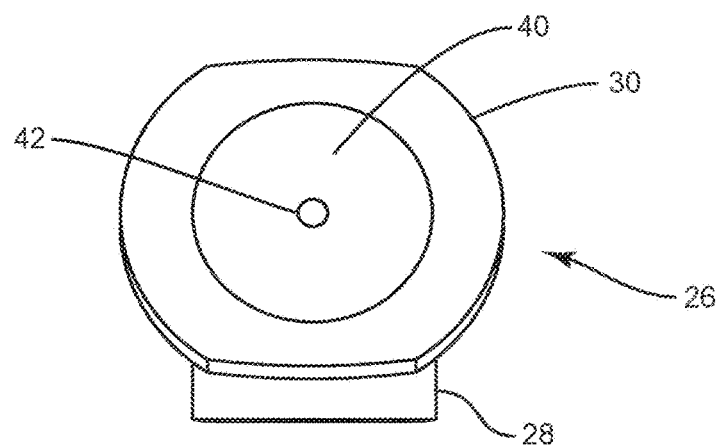
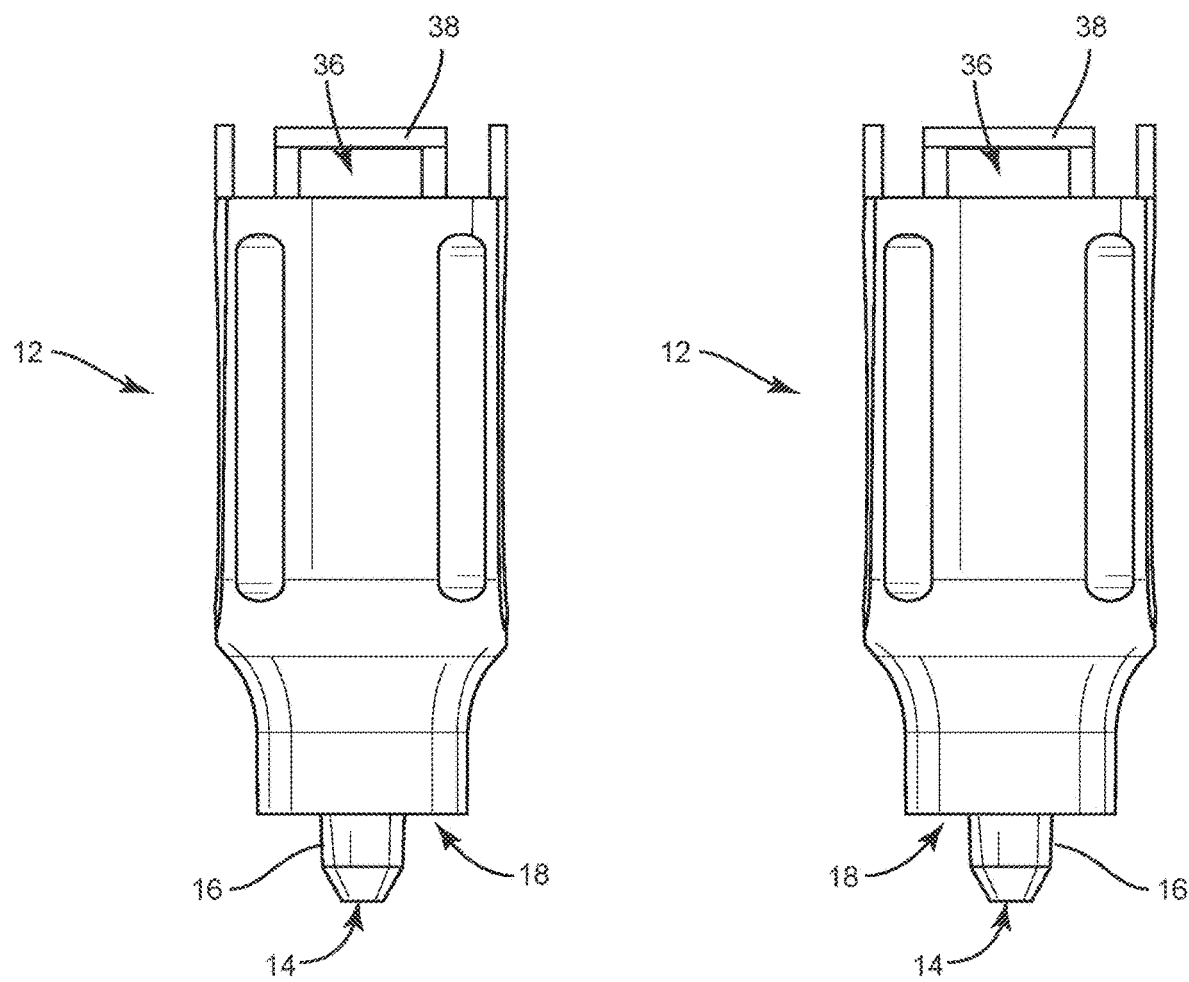
FIG. 6
FIG. 7　　　　FIG. 8

DRUG DEPOT DELIVERY SYSTEM AND METHOD

CROSS-REFERENCE TO RELATED APPLICATIONS

This application is a continuation of U.S. patent application Ser. No. 16/590,654, filed Oct. 2, 2019 and issued as U.S. Pat. No. 11,478,587, which is a continuation of U.S. patent application Ser. No. 15/345,764, filed on Nov. 8, 2016 and issued as U.S. Pat. No. 10,434,261.

TECHNICAL FIELD

The present disclosure generally relates to drug delivery devices, and more particularly to a drug pellet delivery system that includes features that prevent drug pellets from being misdirected as they move through a drug delivery device.

BACKGROUND

Drugs may be delivered to patients by a variety of methods including oral, intravenous, intramuscular, inhalation, topical or subcutaneous delivery. The drug may be delivered directly or locally to the treatment site (e.g., intrathecally, intraspinally, intraarticularly, etc.). The method of delivery chosen depends upon, among other things, the condition being treated, and the desired therapeutic concentration of the drug to be achieved in the patient and the duration of drug concentration that must be maintained.

Drug pellets, such as, for example, drug depots have been developed, which allow a drug to be introduced or administered to sites beneath the skin of a patient. The drug depot releases the drug over a period of time. Drug depots allow the drug to be released from the depot in a relatively uniform dose over weeks, months or even years. Administering drugs using drug depots is becoming especially important and popular in modulating the immune, inflammation and/or pain responses in treatment of chronic conditions including rheumatoid arthritis, osteoarthritis, sciatica, carpal tunnel syndrome, lower back pain, lower extremity pain, upper extremity pain, cancer, tissue pain and pain associated with injury or repair of cervical, thoracic, and/or lumbar vertebrae or intervertebral discs, rotator cuff, articular joint, TMJ, tendons, ligaments, muscles, and the like.

Drug delivery devices have been developed to implant drug depots within a patient. These devices have a cartridge that contains one or more drug depots. A rod is moved within the cartridge to push the drug depot out of the cartridge. However, the drug depots can be misdirected as they are pushed through the cartridge by the rod. In some cases, the drug depots have the potential to lift and escape a pathway of the cartridge, thus preventing the drug depots from being properly expelled from the cartridge or, in some cases, from being expelled at all. This disclosure describes improvements over these prior art technologies.

SUMMARY

In one embodiment, a drug pellet delivery system is provided. The drug pellet delivery system includes a housing having a cavity. A cartridge is positioned within the cavity and includes a body having a channel. One or a plurality of drug pellets, such as, for example, drug depots may be positioned within the channel. The body includes a first pair of rails and a second pair of rails on opposite sides of the channel. A plunger is slidably disposed through the housing and the channel. The plunger includes a push rod to move the drug depots through the channel and out of the housing. The rails are configured to prevent the drug depots from being misdirected as the drug depots move through the channel. In some embodiments, kits and methods of use are disclosed.

BRIEF DESCRIPTION OF THE DRAWINGS

The present disclosure will become more readily apparent from the specific description accompanied by the following drawings, in which:

FIG. 1 is a front view of one embodiment of components of a drug pellet delivery system in accordance with the present principles of the present disclosure;

FIG. 1A is a front view, in part phantom, of components of the drug pellet delivery system shown in FIG. 1.

FIG. 6 is an end, perspective view of a component of the drug pellet delivery system shown in FIG. 1;

FIG. 7 is a left side view of a component of the drug pellet delivery system shown in FIG. 1; p FIG. 8 is a right side view of a component of the drug pellet delivery system shown in FIG. 1;

Like reference numerals indicate similar parts throughout the figures.

DETAILED DESCRIPTION

Figures 2, 3:
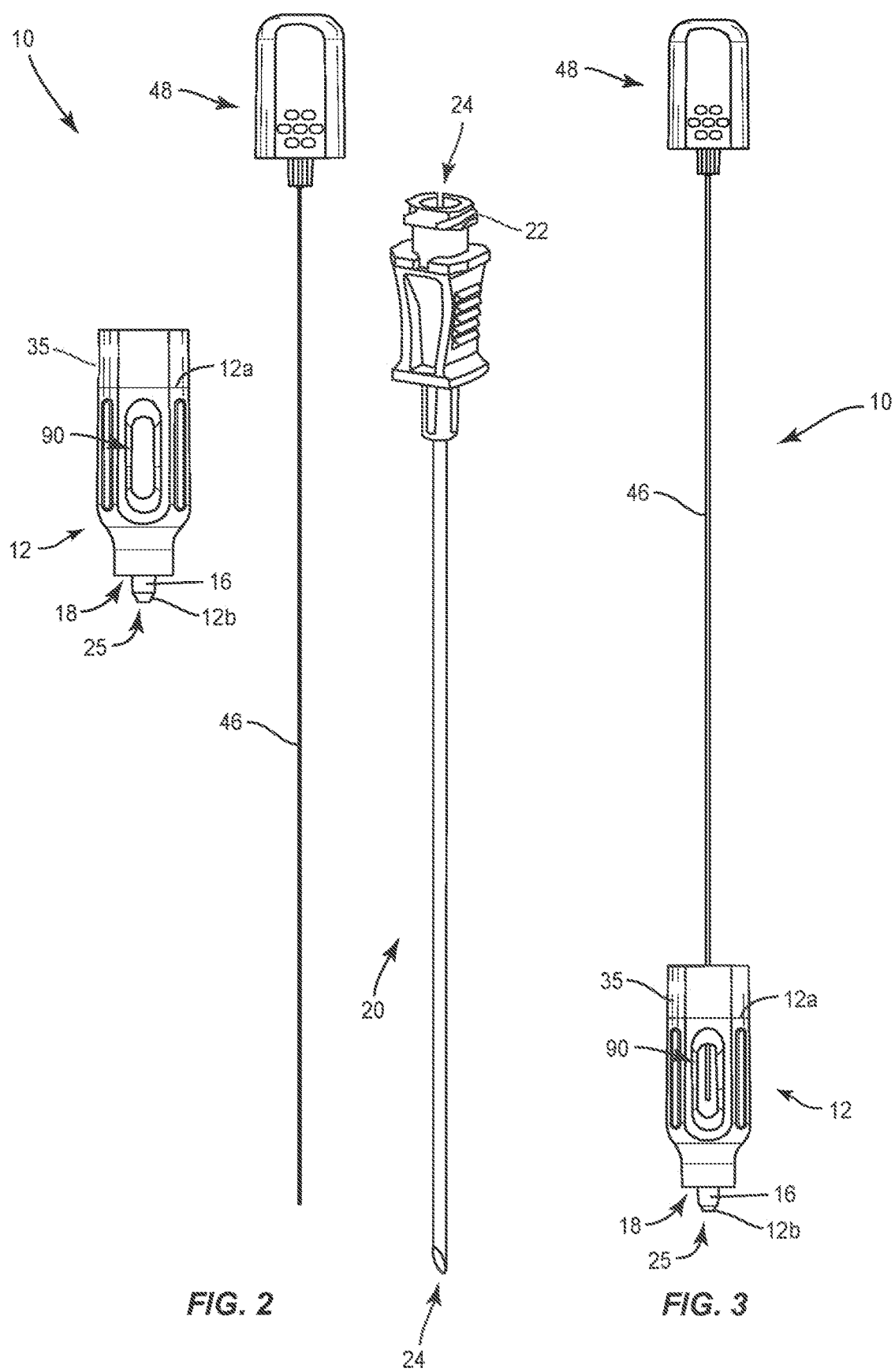
FIG. 2 is a front view of the drug pellet delivery system shown in FIG. 1, with parts separated.
FIG. 3 is a front view of the drug pellet delivery system shown in FIG. 1.

The exemplary embodiments of a drug pellet delivery system and related methods are discussed in terms of medical devices for delivering drug pellets, such as, for example, one or a plurality of drug depots. In some embodiments, the system and method may be employed in applications that require at least one drug depot to be implanted within a patient's body.

In some embodiments, the drug pellet delivery system includes a cartridge having directional rails that block and redirect a delivery plunger and drug depots or pellets to maintain alignment through a pellet pathway of the cartridge. In some embodiments, the cartridge includes upper and lower directional rails. In some embodiments, the upper directional rails maintain the directional alignment of the delivery plunger and the lower directional rails maintain the directional alignment of the drug depots or pellets during deployment. It has been found that the directional rails substantially improve the function of the drug pellet delivery system facilitating better deployment of the drug depots or pellets and preventing jamming of the delivery plunger and/or the drug depots or pellets.

In some embodiments, one or all of the components of the drug pellet delivery system may be disposable, peel-pack, pre-packed sterile devices. In some embodiments, the components of the drug pellet delivery system are configured for one time use and are disposed after they are used one time. However, it is contemplated that one or all of the components of the drug pellet delivery system may be reusable. The drug pellet delivery system may be configured as a kit with multiple sized and configured components, including, for example, various drug pellets or depots. In some embodiments, the drug pellets or depots are pre-loaded into a delivery device. In some embodiments, one or more of the components of the drug pellet delivery system are configured to be sterilized.

In some embodiments, the disclosed drug pellet delivery system and methods may be alternatively employed in a surgical treatment with a patient in a prone or supine position, and/or employ various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drug pellets or drug depots to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a drug pellet delivery system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-13, there are illustrated components of a drug pellet delivery system 10 in accordance with the principles of the present disclosure.

The components of drug pellet delivery system 10 can be fabricated from biologically acceptable materials suitable for medical applications, including metals, synthetic polymers, ceramics and bone material and/or their composites, depending on the particular application and/or preference of a medical practitioner. For example, the components of drug pellet delivery system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TOP), hydroxyapatite (HA)-TCP, calcium sulfate, or other resorbable polymers such as polyaetide, polyglycolide, polytyrosine carbonate, polycaroplaetohe and their combinations. Various components of drug pellet delivery system 10 may have material composites, including the above materials, to achieve various desired characteristics such as strength, rigidity, elasticity, compliance, biomechanical performance, durability and radiolucency or imaging preference. The components of drug pellet delivery system 10, individually or collectively, may also be fabricated from a heterogeneous material such as a combination of two or more of the above-described materials. The components of drug pellet delivery system 10 may be monolithically formed, integrally connected or include fastening elements and/or instruments, as described herein.

In some embodiments, drug pellet delivery system 10 is used to deliver one or a plurality of drug pellets or drug depots. In some embodiments, the drug pellet or drug depots may include an active agent, such as, for example, one or a plurality of drugs.

Drug pellet delivery system 10 includes a housing 12 having an inner surface that defines a cavity 14. Housing 12 includes openings that extend through opposite proximal and distal end surfaces 12a, 12b of housing 12. The openings are in communication with cavity 14. In some embodiments, a distal end of housing 12 includes a nozzle 16 and an aperture 18 defined by an inner surface of housing 12 and an outer surface of nozzle 16. Aperture 18 is spaced apart from cavity 14 by a wall such that aperture 18 is not in communication with cavity 14. The inner surface of housing 12 that defines a portion of aperture 18 is threaded such that a hollow tube, such as, for example, cannula 20 shown in FIG. 2 can be positioned over nozzle 16 such that threads of cannula 20 engage the threaded inner surface of housing 12 that defines a portion of aperture 18 to couple cannula 20 to housing 12. In some embodiments, nozzle 16 is positioned within cannula 20 and cannula 20 is rotated relative to housing 12 to mate threads of cannula 20 with the threaded inner surface of housing 12 that defines a portion of aperture 18 to couple cannula 20 to housing 12. In some embodiments, cannula 20 can be variously connected with housing 12, such as, for example, monolithic, integral connection, frictional engagement, threaded engagement, mutual grooves, screws, adhesive, nails, barbs and/or raised elements. Nozzle 16 includes a conduit 25 that is in communication with cavity 14 and extends entirely through nozzle 16. Conduit 25 is coaxial with cavity 14. In some embodiments, conduit 25 has a circular cross sectional configuration. In some embodiments, conduit 25 may have various cross section configurations, such as, for example, oval, oblong, triangular, rectangular, square, polygonal, irregular, uniform, non-uniform, variable, tubular and/or tapered.

Figure 4:
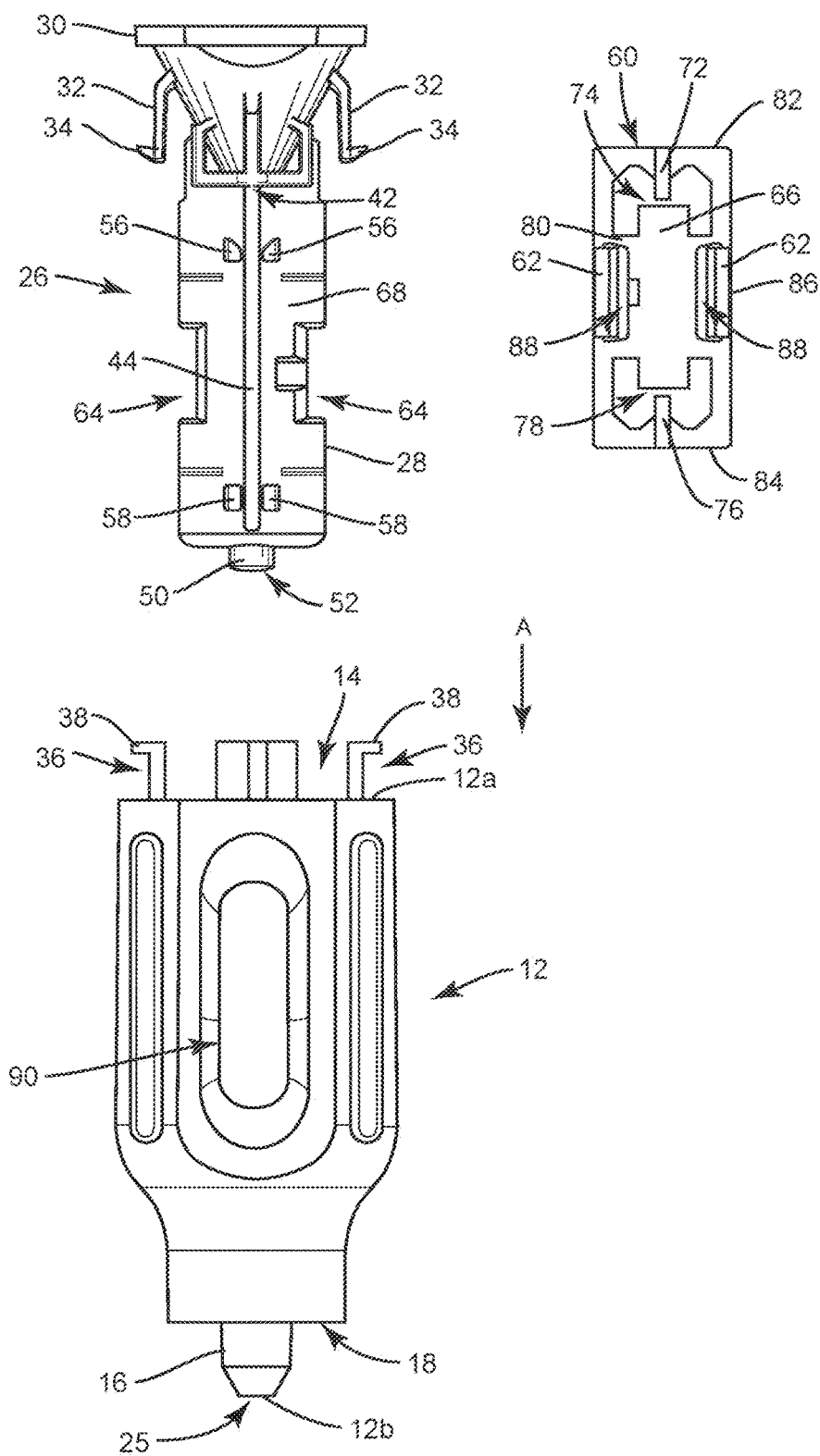
FIG. 4 is a front view of components of the drug pellet delivery system shown in FIG. 1, with parts separated.
Figure 5:
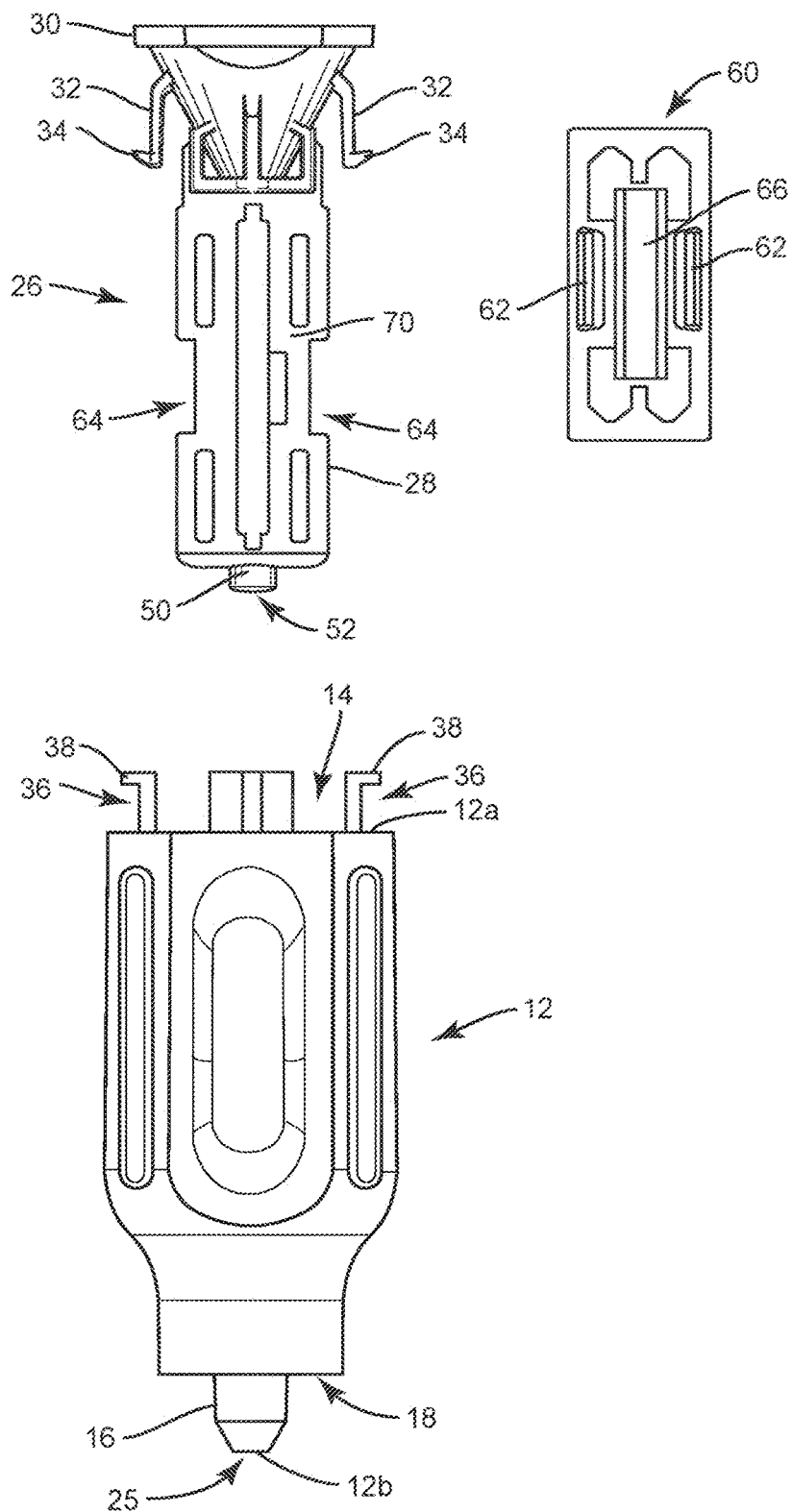
FIG. 5 is a back view of components of the drug pellet delivery system shown in FIG. 1, with parts separated.

A cartridge 26 is positioned within cavity 14. Cartridge 26 comprises a body 28 and a funnel portion 30 coupled to a proximal end of body 28, as shown in FIGS. 4 and 5. In some embodiments, funnel portion 30 is integrally formed with body 28. That is, cartridge 26 is monolithic such that funnel portion 30 is permanently fixed to body 28 and cannot be removed from body 28 without breaking funnel portion 30 and/or body 28. In some embodiments, funnel portion 30 comprises a pair of tabs, such as, for example, extensions 32 that each include a barb 34. Barbs 34 are configured to be positioned within openings 36 in tabs, such as, for example, projections 38 of housing 12 to couple cartridge 26 to housing 12 such that cartridge 26 is fixed relative to housing 12. Openings 36 and projections 38 are shown in FIGS. 7 and 8, for example. In some embodiments, extensions 32 are resilient such that extensions 32 can deflect toward and away from funnel portion 30. Barbs 34 are tapered such that cartridge 26 can be inserted into cavity 14 by positioning cartridge 26 above housing 12 and moving cartridge 26 relative to housing 12 in the direction shown by arrow A in FIG. 4. As cartridge 26 moves relative to housing 12 in the direction shown by arrow A in FIG. 4, barbs 34 engage projections 38, which forces extensions 32 inwardly toward funnel portion 30. Cartridge 26 is moved further relative to housing 12 in the direction shown by arrow A in FIG. 4 until barbs 34 are aligned with openings 36, which causes extensions 32 to move outwardly and away from funnel portion 30 to position barbs 34 within openings 36 and fix cartridge 26 relative to housing 12. In some embodiments, extensions 32 are biased outwardly, away from funnel portion 30. This prevents barbs 34 from being removed from openings 36. That is, to remove barbs 34 from openings 36, a force must be applied to extensions 32 to force extensions 32 toward one another. When the housing 12 is assembled, extensions 32 are surrounded by a ring 35. Ring 35 also surrounds the funnel portion 30 and sits atop the housing 12 and abuts the proximal portion of the plunger 48. Ring 35 protects the extensions 32 from accidental uncoupling.

Funnel portion 30 comprises a lip that sits atop the ring 35, as shown in FIG. 1, and conical inner surface that defines a tapered cavity 40, as shown in FIG. 6. Funnel portion 30 comprises an opening 42 in the conical inner surface that is in communication with cavity 40. Body 28 comprises a channel 44 that is aligned with opening 42 such that a rod, such as, for example, a push rod 46 of a plunger 48 can be inserted through cavity 40 and opening 42 and enter channel 44. In some embodiments, channel 44 is defined by a concave inner surface of body 28. In some embodiments, channel 44 has a semi-circular cross sectional configuration. In some embodiments, channel 44 is coaxial with cavity 14, conduit 25, cavity 40 and/or opening 42. Body 28 comprises a tip, such as, for example, a nipple portion 50, as shown in FIGS. 4, 5, 9 and 12. An opening or passageway, such as, for example, a lumen 52 extends through nipple portion 50 and is aligned with channel 44 such that push rod 46 can extend through cavity 14, cavity 40, opening 42, channel 44, lumen 52 and conduit 25 simultaneously. Channel 44 is configured to have one or a plurality of drug depots, such as, for example, drug pellets 54 shown in FIGS. 9 and 12 positioned therein. Push rod 46 and drug pellets 54 each have a maximum diameter that is less than or equal to a maximum diameter of conduit 25, opening 42 and lumen 52. The maximum diameter of push rod 46 is equal to or greater than a maximum diameter of drug pellets 54 such that push rod 46 can be inserted through cavity 40 and opening 42. Push rod 46 is moved relative to housing 12 and cartridge 26 in the direction shown by arrow A in FIG. 4 such that a distal end of push rod 46 moves into channel 44. Moving push rod 46 further in the direction shown by arrow A in FIG. 4 causes the distal end of push rod 46 to engage a drug pellet 54 within channel 44 and move the drug pellet 54 out of channel 44 through lumen 52, as discussed herein and shown in FIG. 12. After the drug pellet 54 exits lumen 52, the drug pellet 54 can move through conduit 25 and into passageway 24 of cannula 20 to deliver the drug pellet to a location within a patient, as discussed herein. In some embodiments, drug pellets 54 have a maximum diameter that is equal to or less than a depth of channel 44 such that drug pellets 54 are disposed entirely within channel 44 when drug pellets 54 are positioned within channel 44. In some embodiments, drug pellets 54 have a maximum diameter that is greater than the depth of channel 44 such that a portion of drug pellets 54 extend out of channel 44 when drug pellets 54 are positioned within channel 44. Opening 42 is coaxial with lumen 52 and conduit 25, as discussed herein. In some embodiments, opening 42 and/or lumen 52 have a circular cross sectional configuration. In some embodiments, opening 42 and/or lumen 52 may have various cross section configurations, such as, for example, oval, oblong, triangular, rectangular, square, polygonal, irregular, uniform, non-uniform, variable, tubular and/or tapered.

Figure 9:
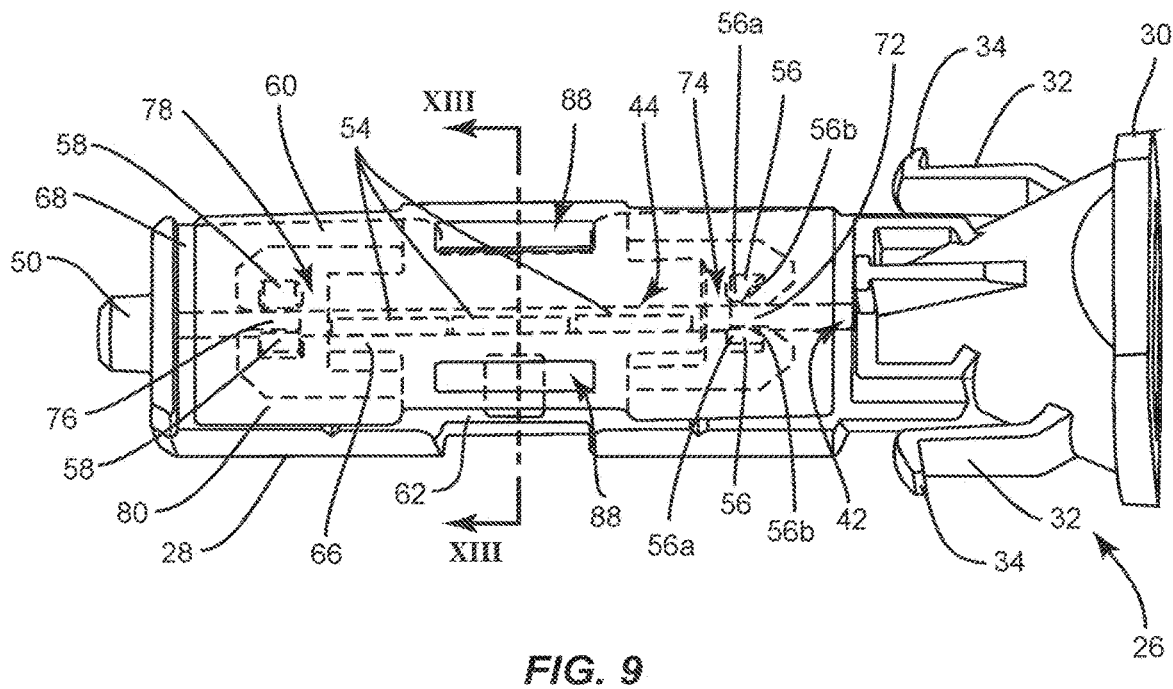
FIG. 9 is a perspective, front view of some of the components of the drug pellet delivery system shown in FIG. 1.
Figure 10:
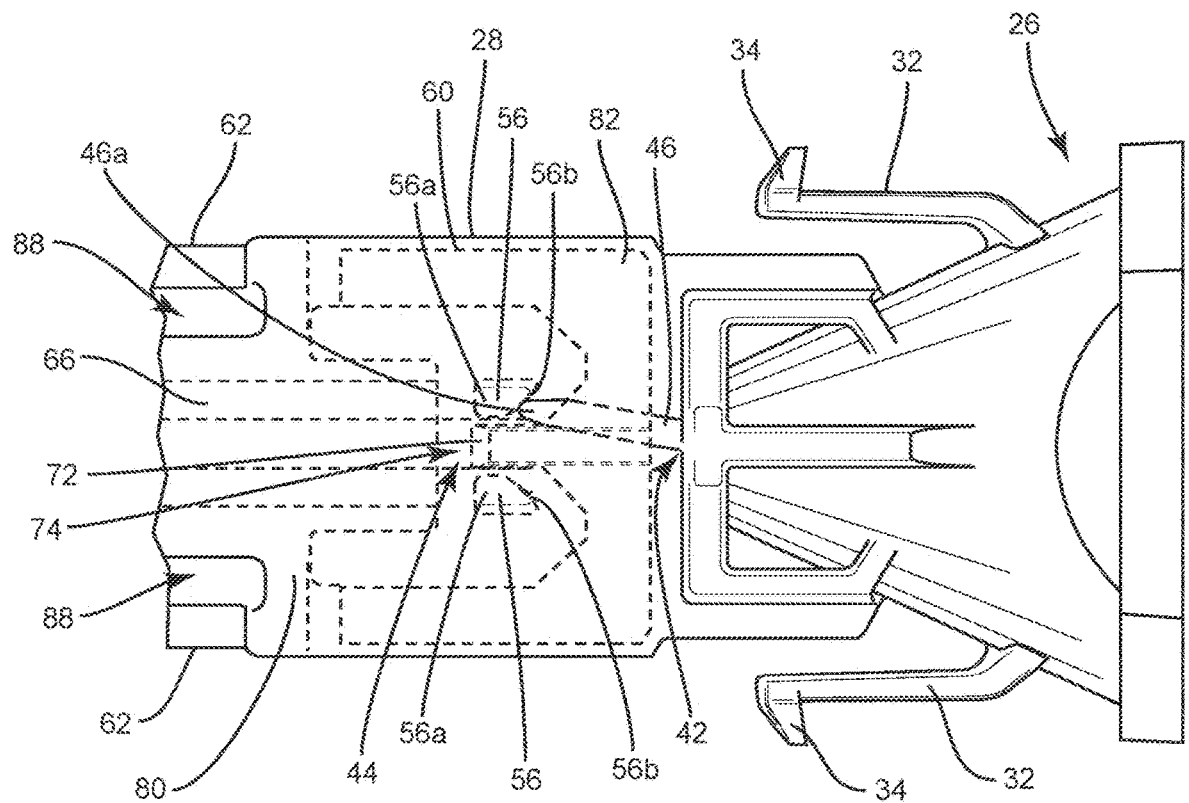
FIG. 10 is a close up, front view of some of the components of the drug pellet delivery system shown in FIG. 1.
Figure 11:
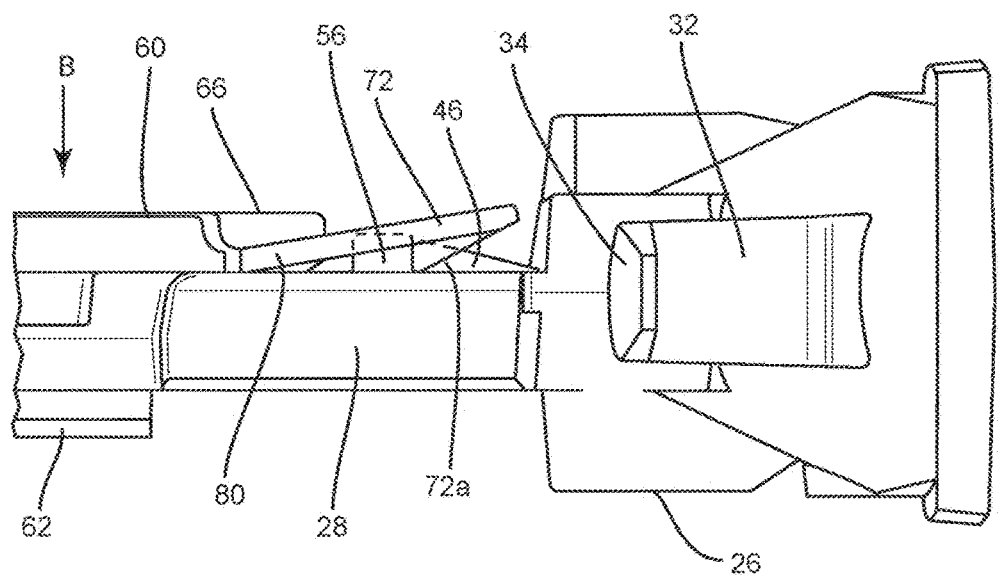
FIG. 11 is a close up, side view of some of the components of the drug pellet delivery system shown in FIG. 1.

In some embodiments, body 28 includes a first pair of directional rails 56, as shown in FIGS. 4, 9, 10 and 12. Rails 56 are positioned adjacent to opening 42 and are spaced apart from one another by channel 44. Rails 56 extend outwardly from an outer surface of body 28 and each include a first portion 56a that extends parallel to a longitudinal axis defined by channel 44 and a second tapered portion 56b. Portions 56b extend transverse to the longitudinal axis defined by channel 44. Portions 56b are each tapered from a proximal end of body 28 to an interface between portions 56a, 56b such that a distance between portions 56b is greater at the proximal end of body 28 than at the interface between portions 56a, 56b. In some embodiments, rails 56 each extend parallel to the longitudinal axis defined by channel 44 along the entire length of rails 56. Rails 56 are configured to block and redirect push rod 46 of plunger 48 to maintain alignment of push rod 46 through channel 44, as shown in FIGS. 10 and 11. That is, rails 56 prevent push rod 46 from falling out of channel 44 as push rod 46 moves within channel 44 in direction A shown FIG. 4. For example, if push rod 46 is inserted through opening 42 and into channel 44 such that push rod 46 extends transverse to the longitudinal axis defined by channel 44, a distal tip 46a of push rod 46 will engage an inner surface of one of portions 56b, as shown in FIG. 10. As push rod 46 moves within channel 44 in direction A shown FIG. 4, portions 56b will redirect push rod 46 between portions 56a such that push rod 46 is oriented parallel to the longitudinal axis defined by channel 44. In some embodiments, tip 46a of push rod 46 is blunt so as to prevent damage to drug pellets 54.

Figure 12:
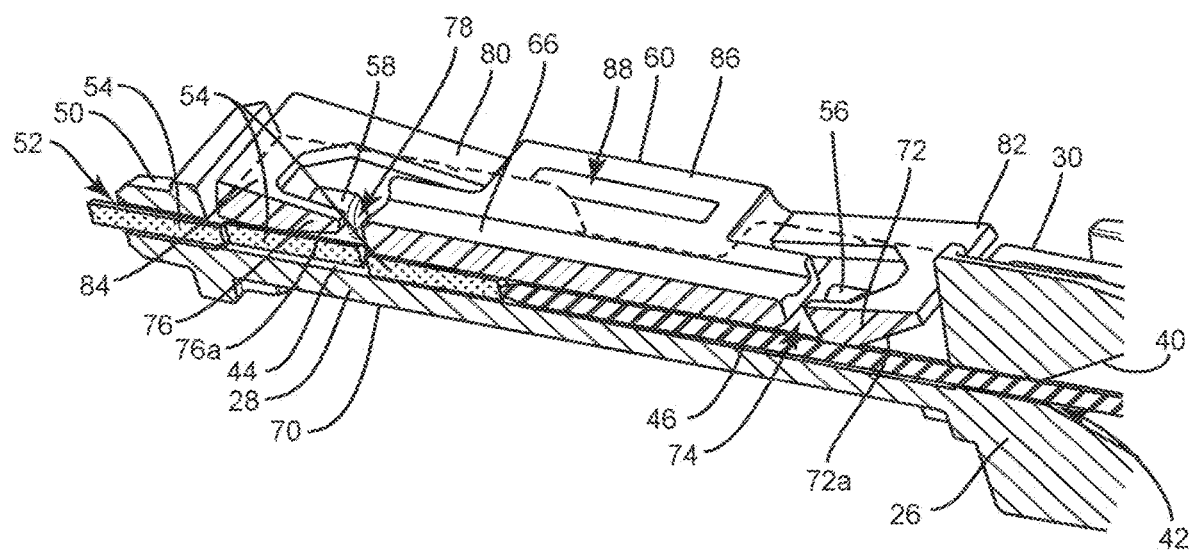
FIG. 12 is a perspective, side, cross section view of some of the components of the drug pellet delivery system shown in FIG. 1.
Figure 13:
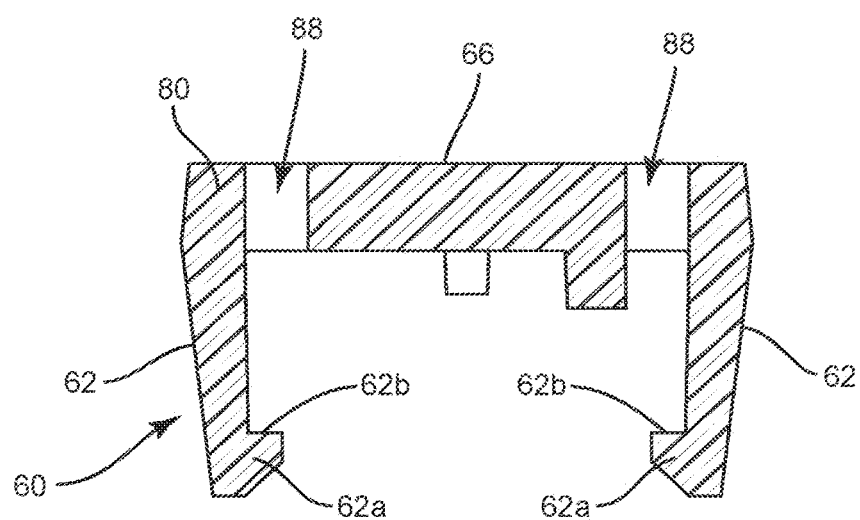
FIG. 13 is an end, cross section view of a component of the drug pellet delivery system shown in FIG. 1 taken along lines XIII-XIII in FIG. 9.

In some embodiments, body 28 includes a second pair of directional rails 58, as shown in FIGS. 4, 9 and 12. Rails 58 are positioned adjacent to nipple portion 50 and are spaced apart from one another by channel 44. Rails 58 each extend outwardly from the outer surface of body 28 and each extend parallel to the longitudinal axis defined by channel 44 along the entire length of rails 58. Rails 58 are configured to block and redirect drug pellets 54 to maintain alignment of drug pellets 54 through channel 44, as shown in FIG. 12. That is, rails 58 prevent drug pellets 54 from falling out of channel 44 (e.g., move laterally) as drug pellets 54 move within channel 44 in direction A shown FIG. 4. For example, if drug pellets 54 begin to move laterally within channel 44, drug pellets 54 will engage inner surfaces of rails 58 to redirect drug pellets 54 between rails 58 such that drug pellets 54 are positioned within channel 44. This maintains alignment of drug pellets 54 with channel 44 such that drug pellets 54 are aligned with lumen 52 such that push rod 46 can push drug pellets 54 through channel 44 and out of cartridge 26 through lumen 52. In some embodiments, rails 58 are shaped and configured similar to rails 56 described herein. That is, rails 58 may each include a portion that is parallel to the longitudinal axis defined by channel 44 and a tapered portion that extends transverse to the longitudinal axis defined by channel 44.

In some embodiments, a cover 60 is removably coupled to cartridge 26 to assist in maintaining drug pellets 54 within channel 44. Cover 60 comprises a pair of tabs 62 that are positioned within grooves 64 in body 28 to attach cover 60 to cartridge 26. Tabs 62 extend outwardly from a frame 80 of cover 60. A wall 66 of cover 60 is configured to be positioned over channel 44 such that wall 66 covers at least a portion of channel 44 to maintain drug pellets 54 within channel 44. Wall 66 engages a front surface 68 of body 28. Front surface 68 is shown in FIG. 4, for example. Channel 44 extends into front surface 68 and rails 56, 58 each extend outwardly from front surface 68. In some embodiments, tabs 62 are resilient such that tabs 62 can deflect toward and away from wall 66 and/or frame 80. In some embodiments, tabs 62 each include a tapered barb 62a having a surface 62b that engages a back surface 70 (FIG. 5) of body 28 when wall 66 engages front surface 68. Back surface 70 is opposite front surface 68. A distance between wall 66 and surface 62b is slightly greater than a distance between front surface 68 and back surface 70 such that cover 60 can be coupled to body 28 by positioning cover 60 above cartridge 26 with tabs 62 aligned with grooves 64. Cover 60 is moved relative to body 28 in the direction shown by arrow B in FIG. 11. As cover 60 moves relative to body 28 in the direction shown by arrow B in FIG. 11, barbs 62a engage front surface 68, which forces tabs 62 outwardly such that a distance between barbs 62a increases. Cover 60 is moved further relative to body 28 in the direction shown by arrow B in FIG. 11 such that barbs 62a move along a side surface of body 28 that extends between front and back surfaces 68, 70. As barbs 62a move passed the side surface of body 28, tabs 62 move inwardly to decrease the distance between barbs 62a such that surfaces 62b engage back surface 70 to fix cover 60 relative to body 28. In some embodiments, tabs 62 are biased inwardly, toward one another such that tabs 62 snap into place about cartridge 26 as cover 60 is moved relative to cartridge 26 in the direction shown by arrow B in FIG. 11 as described above.

In some embodiments, cover 60 includes a projection 72 having a tip that is spaced apart from wall 66 by a gap 74 and a projection 76 having a tip that is spaced apart from wall 66 by a gap 78, as shown in FIGS. 4, 9 and 12. Projections 72, 76 are connected to wall 66 by frame 80, as best shown in FIG. 9. Tabs 62 extend outwardly from frame 80. In some embodiments, gaps 74, 78 allow opposite proximal and distal ends 82, 84 of frame 80 to deflect relative to a middle portion 86 of frame 80, as shown in FIG. 12, for example. Tabs 62 extend from middle portion 86.

Cover 60 is positioned relative to cartridge 26 such that when wall 66 of cover 60 engages front surface 68 of body 28, projection 72 is positioned between rails 56 and projection 76 is positioned between rails 58. In some embodiments, projection 72 includes a ramp 72a that is tapered from the tip of projection 72 to proximal end 82 of frame 80 and projection 76 includes a ramp 76a that is tapered from distal end 84 of frame 80 to the tip of projection 76, as best shown in FIG. 12.

Ramp 72a is configured to redirect tip 46a of push rod 46 into channel 44 should push rod 46 be inserted through opening 42 and into channel 44 in a direction that is transverse to the longitudinal axis defined by channel 44, as shown in FIG. 11, for example. That is, if push rod 46 is inserted into channel 44 in a direction that is transverse to the longitudinal axis defined by channel 44, push rod will engage ramp 72a such that proximal end 82 of frame 80 deflects upwardly relative to middle portion 86 of frame 80 such that proximal end 82 extends transverse to middle portion 86. Tip 46a will slide along ramp 72a to guide push rod 46 into channel 44 such that push rod 46 is coaxial with channel 44. In some embodiments, proximal end 82 extends transverse to middle portion 86 when push rod 46 is positioned within channel 44, as shown in FIG. 12. In some embodiments, once push rod 46 is coaxial with channel 44, proximal end 82 will move relative to middle portion 86 such that proximal end 82 extends parallel to middle portion 86. As such, rails 56 prevent push rod 46 from moving laterally within channel 44 and projection 72 prevents push rod 46 from moving upwardly out of channel 44 to orient push rod 46 such that push rod 46 is coaxial with channel 44 as push rod 46 moves through channel 44.

Ramp 76a is configured to redirect drug pellets 54 into channel 44 should drug pellets 54 begin to lift out of channel 44. That is, if drug pellets 54 move within channel 44 such that drug pellets 54 are transverse to the longitudinal axis defined by channel 44, drug pellets 54 will engage ramp 76a such that distal end 84 of frame 80 deflects upwardly relative to middle portion 86 of frame 80 such that distal end 84 extends transverse to middle portion 86, as shown in FIG. 12. Drug pellets 54 will slide along ramp 76a to guide drug pellets 54 into channel 44 such that drug pellets 54 are coaxial with channel 44. In some embodiments, distal end 84 extends transverse to middle portion 86 when drug pellets 54 are positioned within channel 44, as shown in FIG. 12. In some embodiments, once drug pellets 54 are coaxial with channel 44, distal end 84 will move relative to middle portion 86 such that distal end 84 extends parallel to middle portion 86. As such, rails 58 prevent drug pellets 54 from moving laterally within channel 44 and projection 76 prevents drug pellets 54 from moving upwardly out of channel 44 to orient drug pellets 54 such that drug pellets 54 are coaxial with channel 44 as drug pellets 54 move through channel 44.

In some embodiments, cover 60 includes apertures 88 between wall 66 and tabs 62, as shown in FIGS. 4, 9 and 10, for example. Apertures 88 are spaced apart from one another by wall 66. It is envisioned that apertures 88 allow tabs 62 to deflect inwardly and outwardly relative to wall 66 to increase and decrease the distance between barbs 62a to couple cover 60 to cartridge 26, as discussed herein. Apertures 88 have a substantially rectangular configuration. In some embodiments, apertures 88 may have various configurations, such as, for example, oval, oblong, triangular, rectangular, square, polygonal, irregular, uniform, non-uniform, variable, tubular and/or tapered.

In assembly, operation and use, system 10 is employed with a surgical procedure, such as, to deliver one or more drug pellets or drug depots, such as, for example drug pellets 54 to a target location within a patient.

For example, system 10 and accessories thereof, described above, can be employed to implant one or more drug pellets within a patient at a selected location, such as, for example, a surgical site. In use, a medical practitioner obtains access to the surgical site in any appropriate manner. It is envisioned that system 10 can be used in any existing surgical method or technique including open surgery, mini-open surgery, minimally invasive surgery and percutaneous surgical implantation. One or more drug pellets can be delivered to the target location using system 10.

System 10 may be assembled by inserting one or more drug pellets or drug depots, such as, for example, drug pellets 54 within channel 44. In some embodiments, the drug pellets each include the same drug or combination of drugs. In some embodiments, the drug pellets may include different drugs, different combinations of drugs and/or different amounts of drugs. Cover 60 is coupled to cartridge 26, as discussed herein. In particular, cover 60 is positioned above cartridge 26 with tabs 62 aligned with grooves 64. Cover 60 is moved relative to body 28 in the direction shown by arrow B in FIG. 11. As cover 60 moves relative to body 28 in the direction shown by arrow B in FIG. 11, barbs 62a engage front surface 68, which forces tabs 62 outwardly such that the distance between barbs 62a increases. Cover 60 is moved further relative to body 28 in the direction shown by arrow B in FIG. 11 such that barbs 62a move along the side surface of body 28 that extends between front and back surfaces 68, 70. As barbs 62a move passed the side surface of body 28, tabs 62 move inwardly to decrease the distance between barbs 62a such that surfaces 62b engage back surface 70 to fix cover 60 relative to body 28. This allows cover 60 snaps into place about cartridge 26.

Cartridge 26 and cover 60 are then positioned within cavity 14 of housing 12 to couple cartridge 26 to housing, as discussed herein. In particular, cartridge 26 is positioned above housing 12. Cartridge 26 is moved relative to housing 12 in the direction shown by arrow A in FIG. 4. As cartridge 26 moves relative to housing 12 in the direction shown by arrow A in FIG. 4, barbs 34 engage projections 38, which forces extensions 32 inwardly toward body 28. Ring 35 can be placed adjacent to housing such that barbs 36, projections 38, and extensions 32 are surrounded. Cartridge 26 is moved further relative to housing 12 in the direction shown by arrow A in FIG. 4 until barbs 34 are aligned with openings, which causes extensions 32 to move outwardly away from body 28 to position barbs 34 within openings 36 and fix cartridge 26 relative to housing 12. In some embodiments, cover 60 comprises a clear, transparent or translucent material and housing 12 comprises a window 90 such that push rod 46 and/or one or more of the drug pellets in channel 44 can be viewed through window 90. Window 90 also allows visual confirmation when tip 46a of push rod 46 engages a proximal one of the drug pellets within channel 44. In some embodiments, cannula 20 has a length sufficient to allow at least a portion of housing 12 that includes window 90 to be positioned above the skin while the distal end of cannula 20 is adjacent to the target location. This allows a medical practitioner to visualize movement of push rod 46 and/or drug pellets 54 in channel 44 through window 90.

Cannula 20 is coupled to housing 12, as discussed herein, and shown in FIG. 1A. In particular, cannula 20 is positioned over nozzle 16 such that threads 22 of cannula 20 engage the threaded inner surface of housing 12 that defines a portion of aperture 18 to couple cannula 20 to housing 12. When cannula 20 is coupled to housing 12, passageway 24 is coaxial with cavity 14, cavity 40, opening 42, channel 44, lumen 52 and conduit 25.

Cannula 20 includes a tip that is used to make an incision. Cannula 20 is then positioned through the incision such that the distal end of cannula 20 is positioned adjacent to the selected location to deliver one or more of the drug pellets to the selected location. As discussed above, cannula 20 may have a length that is sufficient to have at least a portion of housing 12 positioned above the incision when the distal end of cannula 20 is positioned adjacent to the selected location. Push rod 46 is positioned within cavity 40 and is moved relative to cartridge 26 and housing 12 in the direction shown by arrow A in FIG. 4 such that push rod 46 moves through opening 42 and into channel 44, as shown in FIG. 3. A medical practitioner can visually confirm that push rod 46 is positioned within channel 44 through window 90, as also shown in FIG. 3. Push rod 46 is advanced in the direction shown by arrow A in FIG. 4 until tip 46a of push rod 46 engages a proximal one of the drug pellets positioned in channel 44, as shown in FIG. 12. A medical practitioner can visually confirm that push rod 46 is engaging the drug pellets within channel 44 through window 90. Push rod 46 is further advanced in the direction shown by arrow A in FIG. 4 to push at least one of the drug pellets in channel 44 through lumen 52 and conduit 25 and into passageway 24 of cannula 20. The drug pellet(s) will move through passageway 24 to deliver the drug pellet to the selected target location for implantation within the patient.

Rails 56 and/or projection 72 maintain alignment of push rod 46 with channel 44 to block or redirect push rod 46 if push rod 46 is inserted into channel 44 in a direction that is transverse to the longitudinal axis defined by channel 44, as discussed herein. In particular, if push rod 46 be inserted through opening 42 and into channel 44 in a direction that is transverse (e.g., lateral) to the longitudinal axis defined by channel 44, the distal tip 46a of push rod 46 will engage the inner surface of one of portions 56b, as shown in FIG. 10. As push rod 46 moves within channel 44 in direction A shown FIG. 4, portions 56b will redirect push rod 46 between portions 56a such that push rod 46 is oriented parallel to the longitudinal axis defined by channel 44. Similarly, if push rod 46 be inserted through opening 42 and into channel 44 such that push rod 46 begins to lift out of channel 44, push rod will engage ramp 72a such that proximal end 82 of frame 80 deflects upwardly relative to middle portion 86 of frame 80 such that proximal end 82 extends transverse to middle portion 86. Tip 46a will slide along ramp 72a to guide push rod 46 into channel 44 such that push rod 46 is coaxial with channel 44.

Rails 58 and/or projection 76 maintain alignment of the drug pellets with channel 44 to block or redirect push the drug pellets if the drug pellets move laterally within channel 44, as discussed herein. In particular, if the drug pellets begin to move laterally within channel 44, the drug pellets will engage inner surfaces of rails 58 to redirect the drug pellets between rails 58 such that the drug pellets are positioned within channel 44. This maintains alignment of the drug pellets with channel 44 such that the drug pellets are aligned with lumen 52 such that push rod 46 can push the drug pellets through channel 44 and out of cartridge 26 through lumen 52. Similarly, if the drug pellets move within channel 44 such that the drug pellets begin to lift out of channel 44, the drug pellets will engage ramp 76a such that distal end 84 of frame 80 deflects upwardly relative to middle portion 86 of frame 80 such that distal end 84 extends transverse to middle portion 86, as shown in FIG. 12. The drug pellets will slide along ramp 76a to guide the drug pellets into channel 44 such that the drug pellets are coaxial with channel 44. This configuration allows push rod 46 to push the drug pellets through channel 44 and lumen 52 and into passageway 24 of cannula 20 without push rod 46 or the drug pellets becoming jammed within channel 44, as discussed herein.

In some embodiments, push rod 46 has a length that is long enough to adequately expel the drug depots through the combined length of housing 12, cartridge 26 and cannula 20. In some embodiments, push rod 46 has a length that is less than the combined length of housing 12 and cannula 20. That is, push rod 46 does not and cannot extend to or beyond the distal tip of cannula 20. In some embodiments, push rod 46 has a length that is greater than or equal to the combined length of housing 12, cartridge 26 and cannula 20 such that push rod 46 can be inserted into cartridge 26 and cannula 20 such that push rod 46 extends entirely through cannula 20. In some embodiments, push rod 46 has a length that is greater than the combined length of housing 12, cartridge 26 and cannula 20 such that push rod 46 can be inserted into cartridge 26 and through cannula 20 such that push rod 46 extends entirely through cannula 20 and out of an opening in a distal tip of cannula 20.

In some embodiments, a kit is provided that includes a plurality of push rods, such as, for example, push rods 46 that have different lengths and/or a plurality of cannulas, such as for example, cannula 20 that have different lengths. For example, in some embodiments, the kit includes a first push rod and a first cannula each having a length configured to deliver a drug depot into a petite patient, where the cannula does not need to penetrate deep into the patient. In some embodiments, the kit includes a second push rod and a second cannula, wherein at least one of the second push rod and the second cannula have a length that is greater than that of the first push rod and/or the first cannula such that the second push rod and the second cannula are configured to deliver a drug depot into a normal patient, where the second cannula needs to penetrate deeper into the patient, than with a petite patient. In some embodiments, the kit includes a third push rod and a third cannula, wherein at least one of the third push rod and the third cannula have a length that is greater than that of the second push rod and/or the second cannula such that the third push rod and the third cannula are configured to deliver a drug depot into an obese patient, where the third cannula needs to penetrate deeper into the patient, than with a normal patient. In some embodiments, the kit includes drug pellets, such as, for example, drug pellets 54 and other drug pellets discussed herein. In some embodiments, the kit includes a drug pellet delivery device, such as, for example a device having a housing (e.g., housing 12), a cartridge (e.g., cartridge 26), a ring 35 and a cover (e.g., cover 60) wherein the device is fully assembled in the kit. That is, the cover and the cartridge are fixed relative to one another and are positioned within a cavity in the housing such that the cartridge and cover are fixed relative to the housing, as discussed herein. In some embodiments, the drug pellets are pre-loaded into the cartridge. In some embodiments, the kit includes one or more cannula (e.g., cannula 20) and one or more plunger (e.g., plunger 48) that may be used in conjunction with the device. The cannula and/or the plunger may have different lengths and/or diameters, as discussed herein.

In some embodiments, at bast one of the components of system 10 can be made of radiolucent materials such as polymers. In some embodiments, cannula 20 is made from a radio opaque material. Radiomarkers may be included for identification under x-ray, fluoroscopy, CT or other imaging techniques.

It is envisioned that the use of image guided technologies may be employed with the aid of the system 10. Upon completion of the procedure, the surgical instruments and assemblies are removed and the incision is dosed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A device for delivering a drug depot, the device comprising:
   a cartridge comprising:
      a surface;
      a depot pathway at least partially defined by an opening extending into the surface in a first direction, the depot pathway having a longitudinal axis, the drug depot being positioned in the depot pathway;
      a first pair of rails protruding from the surface in a second direction opposite the first direction, the first pair of rails spaced apart by and outward of the depot pathway; and
      a second pair of rails protruding from the surface in the second direction, the second pair of rails spaced apart by and outward of the depot pathway, the second pair of rails configured to block and redirect the drug depot to maintain alignment of the drug depot through the depot pathway.

2. The device of claim 1, wherein each rail of the first pair of rails comprises:
a first planar surface parallel to the longitudinal axis of the depot pathway; and
a second planar surface tapered towards the depot pathway.

3. The device of claim 1, wherein each rail of the second pair of rails comprises a planar surface parallel to the longitudinal axis of the depot pathway.

4. The device of claim 1, further comprising a cover removably coupled to the cartridge to assist in maintaining the drug depot in the depot pathway.

5. The device of claim 4, wherein the cover comprises a first projection positioned between the first pair of rails.

6. The device of claim 4, wherein the cover is clear or translucent such that the drug depot in the depot pathway can be viewed through the cover.

7. The device of claim 6, further comprising:
the drug depot, wherein the drug depot comprises a therapeutically effective amount of a drug and a resorbable polymer.

8. The device of claim 1, further comprising the drug depot, wherein the drug depot is a pellet comprising a drug and a resorbable polymer.

9. A device for delivering a drug depot, the device comprising:
a cartridge comprising a first pair of rails configured to block and redirect a delivery plunger and a second pair of rails configured to block and redirect the drug depot to maintain alignment of the delivery plunger and the drug depot through a depot pathway of the cartridge,
wherein the first pair of rails include first and second rails that are spaced apart from one another by the depot pathway,
wherein the second pair of rails is spaced apart by and outward of the depot pathway,
wherein each rail of the second pair of rails comprises a planar surface parallel to a longitudinal axis of the depot pathway, and
wherein the second pair of rails protrudes from a surface of the cartridge; and
a cover removably attached to the cartridge,
wherein the cover comprises a projection between the first pair of rails.

10. The device of claim 9, wherein each of the first and second rails of the first pair of rails comprises a planar surface tapered towards the depot pathway.

11. The device of claim 9, wherein the cover is clear or translucent such that the drug depot in the depot pathway can be viewed through the cover.

12. The device of claim 9, wherein the drug depot is a pellet comprising a drug and a resorbable polymer.

13. A method of delivering a drug depot, the method comprising:
advancing a distal end of a plunger in a channel in a cartridge;
redirecting the plunger by a first pair of rails spaced apart by and outward of the channel to maintain alignment of the plunger through the channel;
further advancing the distal end of the plunger in the channel; and
maintaining alignment of the plunger by a second pair of rails spaced apart by and outward of the channel.

14. The method of claim 13, wherein the channel is at least partially defined by an opening in a surface of the cartridge, wherein the first pair of rails protrudes from the surface, and wherein the second pair of rails protrudes from the surface.

15. The method of claim 14, wherein the drug depot is positioned within the channel, wherein advancing the distal end of the plunger comprises pushing on a proximal end of the drug depot, and wherein the drug depot includes a drug and a resorbable polymer.

* * * * *